United States Patent
Karason

(10) Patent No.: US 7,105,122 B2
(45) Date of Patent: Sep. 12, 2006

(54) PROSTHESIS SOCKET DIRECT CASTING DEVICE HAVING MULTIPLE COMPRESSION CHAMBERS

(75) Inventor: Gudjon G. Karason, Sollentuna (SE)

(73) Assignee: Ossur hf, Reykjavik (IS)

( * ) Notice: Subject to any disclaimer, the term of this patent is extended or adjusted under 35 U.S.C. 154(b) by 259 days.

(21) Appl. No.: 10/679,487

(22) Filed: Oct. 7, 2003

(65) Prior Publication Data
US 2004/0137098 A1    Jul. 15, 2004

Related U.S. Application Data

(60) Provisional application No. 60/416,589, filed on Oct. 8, 2002.

(51) Int. Cl.
*A61F 2/62* (2006.01)
*B29C 43/12* (2006.01)
*B29D 31/00* (2006.01)

(52) U.S. Cl. .............. 264/314; 264/DIG. 30; 425/2; 425/389; 623/901

(58) Field of Classification Search ............... 425/2, 425/389; 264/314, DIG. 30; 623/33, 901
See application file for complete search history.

(56) References Cited

U.S. PATENT DOCUMENTS

| | | | | |
|---|---|---|---|---|
| 1,893,853 | A | * 1/1933 | Tullis ............... | 623/37 |
| 2,634,424 | A | * 4/1953 | O'Gorman .......... | 623/37 |
| 4,300,245 | A | * 11/1981 | Saunders .......... | 623/35 |
| 5,108,456 | A | * 4/1992 | Coonan, III ........ | 623/33 |
| 5,503,543 | A | * 4/1996 | Laghi ............... | 425/2 |
| 5,718,925 | A | 2/1998 | Kristinsson et al. ... | 425/2 |
| 5,885,509 | A | 3/1999 | Kristinsson ........ | 425/2 |
| 6,368,357 | B1 | 4/2002 | Schon et al. ....... | 623/37 |

* cited by examiner

*Primary Examiner*—Robert B. Davis
(74) *Attorney, Agent, or Firm*—Bacon & Thomas PLLC

(57) ABSTRACT

A prosthetic socket casting device includes a base with a forward side from which an expandable bladder surrounding a central casting area extends. The bladder includes a plurality of inner expandable chambers that generally extend along the length of the bladder interior and peripherally surround the central casting area. The inner walls of the chambers are formed of a pliable, fluid impermeable relatively thin sheet material that is distendable upon pressurization of the chamber volumes. The bladder further includes an outer covering or wall formed of a material or construction that limits distention of the bladder outwardly. The chambers may be expanded using pressurized air or other fluid to constrict the central casting area in which a residuum having a settable prosthetic socket material thereon may be placed for molding and curing under pressure. The multiple expandable chambers create a desirable pressure distribution circumferentially around the central casting area.

8 Claims, 3 Drawing Sheets

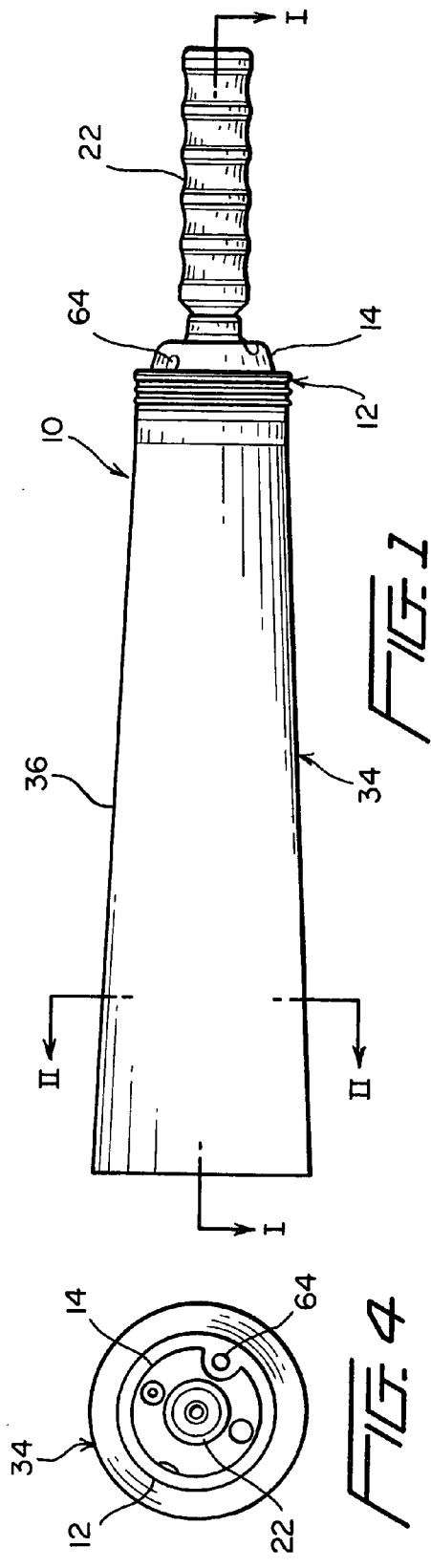
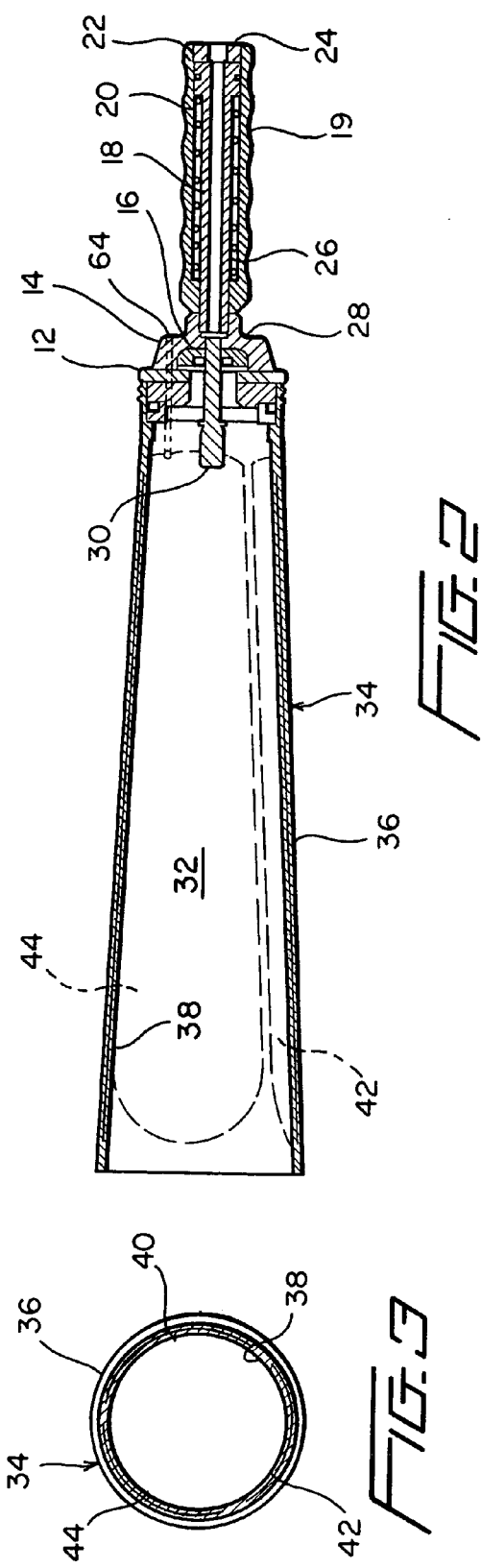

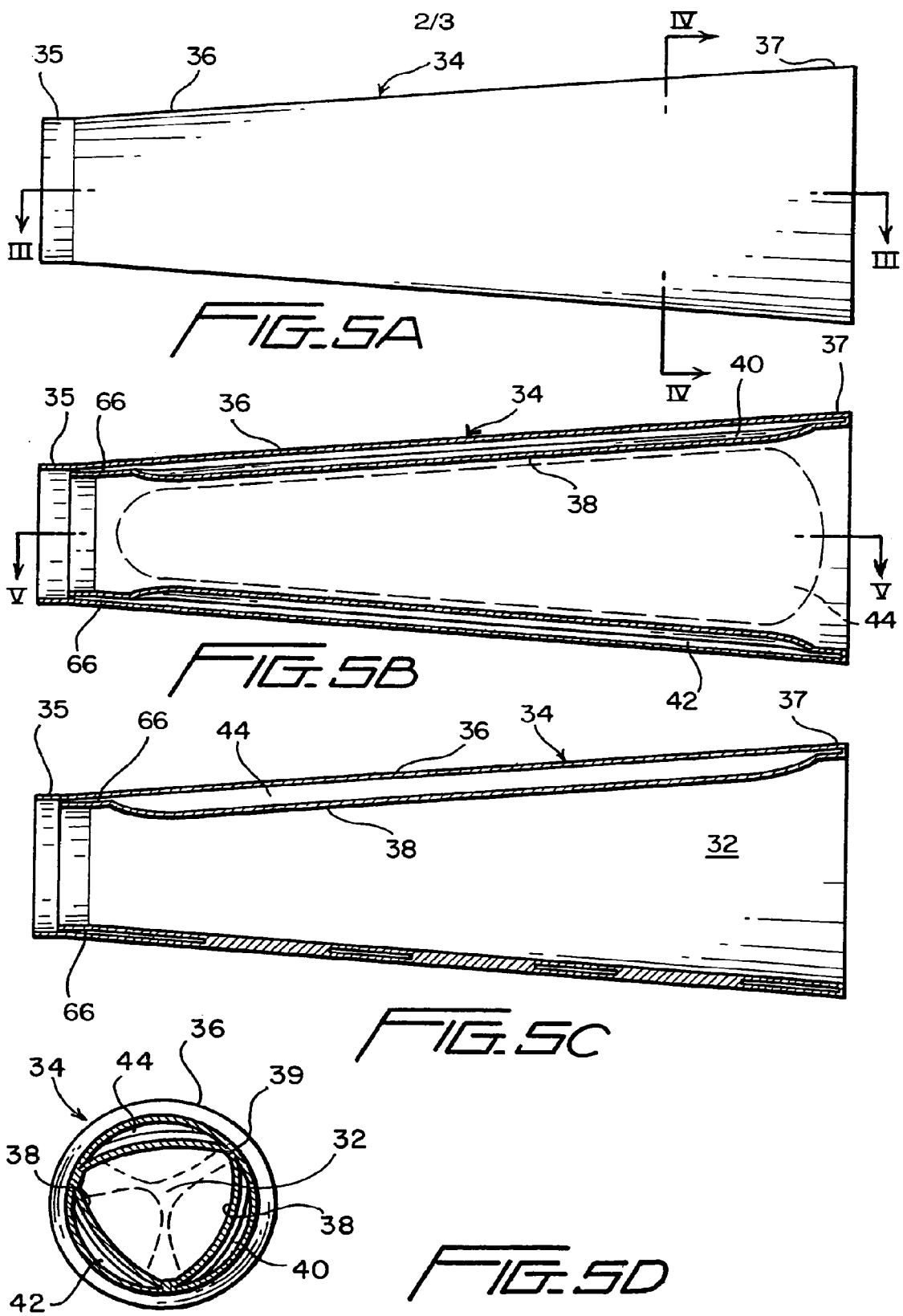

PROSTHESIS SOCKET DIRECT CASTING DEVICE HAVING MULTIPLE COMPRESSION CHAMBERS

This application claims the benefit of Provisional Patent Application Ser. No. 60/416,589 filed Oct. 8, 2002.

BACKGROUND OF THE INVENTION

1. Field of the Invention

This invention relates to a casting device for directly forming or casing prosthesis sockets on residual limbs. More particularly, the invention relates to a casting device that may be placed directly on a residuum to pressurize a moldable and settable prosthesis socket material previously applied over the residuum to thereby produce a socket of finished internal volume.

2. Background of Related Art

Residual limb prosthesis hard sockets have been formed using various techniques, including plaster of paris molds, computer modeling, vacuum forming and various other techniques known to prosthetists. A prior art technique is also known where a prosthesis socket is directly cast on a residuum using a portable pressure casting system, this system being described in U.S. Pat. No. 5,718,925. This technique enables direct pressure casting of a prosthesis socket on a residual limb while tension is applied to the distal area of the residual limb to thereby produce a definitive socket requiring minimum finishing and adjustment upon completion of the casting procedure.

Another version of a direct pressure casting system is described in U.S. Pat. No. 5,885,509, whereby a portable annular pressure casting bladder is rolled over a residuum with a settable socket material thereon and the prosthesis socket is molded and hardened under pressure on the residuum while the residuum is tensioned and elongated during the molding process.

It has been observed that such procedures known in the prior art can be improved to provide better control over distribution of casting pressure during the prosthesis socket molding procedure to yield an improved prosthesis socket having a better fit on the residuum upon completion of the molding procedure.

The present invention is intended to provide an improvement over known prior art systems and in particular, over direct casting systems using a single annular bladder for compressing prosthesis socket material on a residuum during a molding procedure.

BRIEF SUMMARY OF THE INVENTION

The present invention is a prosthesis socket casting device of the type described in U.S. Pat. No. 5,885,509 which is incorporated herein in its entirety by reference. More specifically, the present invention is a portable prosthesis direct casting device, including a base on which is mounted an elongated pliable annular molding bladder having a plurality of expandable chambers that peripherally surround a centrally located casting area. The bladder may be rolled back toward the base or forwardly of the base to permit a residuum to be located in the casting area within the bladder with its associated expandable chambers enveloping the residuum.

The chambers are made of a pliable, fluid impermeable, thin sheet material that, when expanded by internal pressure, flex inwardly towards the central casting area to pressurize a residuum in the casting area with a prosthesis socket material already applied to the external distal area of the residuum. The expandable chambers may be individually or collectively pressurized in a manner to produce inwardly directed forces about the periphery of the residuum and its associated socket casting material during molding and setting (curing) of the socket material. The chambers may include a radially inward facing wall made of elasticized thin sheet material.

In the manner described in U.S. Pat. No. 5,885,509, a suction socket typically formed of silicone or the like, is placed on the residuum before application of the prosthetic socket molding material, with a locking pin installed on the suction sleeve extending distally from the distal end of the suction sleeve. The locking pin cooperates with the base to secure the distal end of the suction sleeve against movement relative to the base or in a manner whereby the pin may be pulled axially in a distal direction to elongate the suction sleeve and the distal end area of the residuum during molding of the prosthetic socket material under pressure from the expandable chambers.

The base includes a lock device for engaging the locking pin and securing same relative to the base or relative to a traction device capable of exerting a tractile force on the locking pin in a distal direction relative to the bladder and its associated expandable chambers.

The base includes appropriate conduits and valves for enabling transmittal of pressurized air or other fluid into the interiors of the expandable chambers to cause their expansion inwardly toward the central casting area during a molding (casting) procedure.

The configuration and orientation of the multiple expandable chambers is selected to provide desired pressure distribution over the prosthesis socket material being molded to a residuum to thereby ensure a proper fit of the molded and hardened socket on the residuum with little or no adjustment required by the prosthetist.

In a preferred embodiment, three longitudinally extending, circumferentially spaced expandable chambers are provided on the interior of the bladder. In an alternate embodiment, a plurality of internal, longitudinally extending, circumferentially spaced expandable chambers may be surrounded by a single annular expandable bladder, with each one or groups of the bladders pressurizable independently of each other or with all bladders in fluid communication with each other.

The bladder preferably includes an outer fabric covering, for example, an elasticized fabric, that controls or prevents outward distention of the outer wall of the bladder when the expandable chambers are pressurized. This ensures that the force of the expandable chambers is directed inwardly toward the casting area and not outwardly away from the casting area.

A hand pump may be associated with the casting device in the manner disclosed in U.S. Pat. No. 5,885,509.

BRIEF DESCRIPTION OF THE DRAWINGS

FIG. 1 is a side elevational view of an embodiment of the prosthesis socket casting device according to the present invention FIG. 2 is a sectional view taken along the line I of FIG. 1;

FIG. 3 is a cross-sectional view taken along line II—II of FIG. 1;

FIG. 4 is an end view of the base member of the casting device showing an air passage;

FIG. 5A is a side elevational view of a bladder constructed in accordance with a first embodiment of the invention;

FIG. 5B is a section view taken along line III—III of FIG. 5A;

FIG. 5C is a sectional view taken along line V—V of FIG. 5B;

FIG. 5D is a cross-sectional view taken along line IV—IV of FIG. 5A;

DETAILED DESCRIPTION OF PREFERRED EMBODIMENTS OF THE INVENTION

Figure 6A:
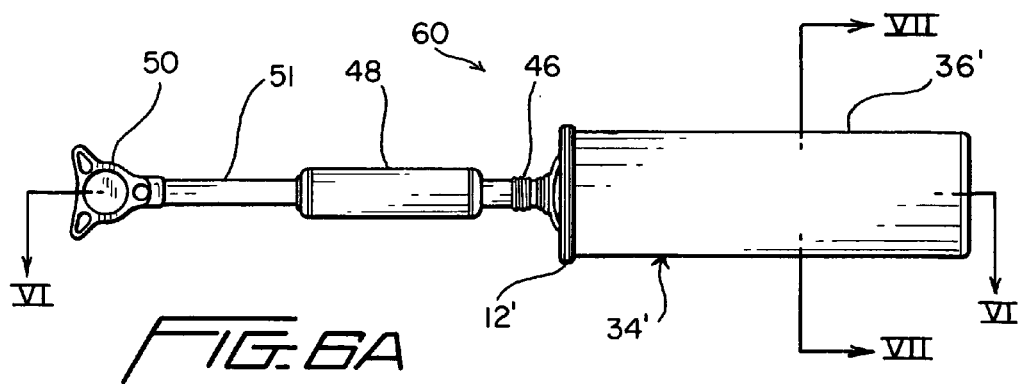
FIG. 6A is a side elevational view of a second embodiment of the casting device constructed in accordance with the invention.

With reference to FIGS. 1 and 2, a prosthesis socket casting device 10 includes a base member 12 which incorporates a lock device 16 that cooperates with a locking pin 28 having a threaded end 30 connectable with the distal end of a suction sleeve 62 (see FIG. 7) donned on a residuum before the casting device is placed in a casting position.

The suction socket is described in U.S. Pat. Nos. 5,718,925 and 5,885,509 and typically comprises a highly pliable silicone elastomer socket having an end structure that includes a threaded socket for receiving the threaded end 30 of a locking pin of the type shown at 28. Suction sockets are used to connect a hard prosthesis socket with a residuum through a vacuum connection and typically are connected with a socket by a locking pin such as pin 28. A suction socket is utilized with the present invention to provide a covering for the residuum over which the prosthesis socket molding material is applied so that the suction socket provides a spacer between the residuum and the finished prosthesis socket that results in production of a correct internal volume within the prosthesis socket that allows for the volume of the suction socket when the prosthesis socket is worn by the amputee with a suction sleeve.

In addition, as disclosed in U.S. Pat. No. 5,885,509, use of the suction socket over the residuum and under the prosthesis socket casting material enables a locking pin 28 to be secured to the distal end of the suction socket and to be connected to the base 12 of the casting device 10. Securing the locking pin to the base 12 results in a tractive force being applied to the distal end of the residuum during casting, as described in U.S. Pat. No. 5,885,509 and to be discussed in more detail below.

In accordance with the embodiment of the invention shown in FIGS. 1 and 2, the pin 28 may be secured against axial movement relative to a connector 14 which releasably engages the pin 28 to secure the pin against movement in a proximal direction relative to the base 12. The connector 14 may be rigidly secured to the base 12 if desired or, optionally, may be associated with a pulling handle 22 that may be manipulated by a prosthetist to pull pin 28 in a distal direction during use of the casting device 10.

In accordance with this example, upon connection of pin 28 via end 30 to a suction socket that has been placed over a residuum, and assuming that the base 12, and bladder 34 (to be described below) remain located relative to a residuum and a suction liner contained within the casting area 32 to be described below, application of tension through handle 22 is transferred through a spring 19 located on spring seating 18 to slider rod 26 and to connector 14 which is connected to pin 28 via lock device 16 that is securable to pin 28. Base 12 is axially movable relative to pin 28 so that effectively pin 28, connector 14 and bar 20 are movable axially relative to base 12 under the constraint of the spring 19 on spring seat 18, that reacts the applied tension force into the handle member 22. Expressed differently, axial force applied toward the right in FIGS. 1 and 2 through handle 22 is transmitted to a compression spring 19 located on spring seat 18 within the handle 22, which in turn is transmitted to slider bar 20 via the enlarged end of the bar shown to the right in FIG. 2, and then transmitted into the base 14 through the connection between the bar 20 and the base 14. The axial load applied to connector 14 is then transmitted through the lock 16 into the pin 28 to enable the force to be applied to the pin 28 independently of the base 12. The degree to which handle 22 moves relative to the slider bar 20 (i.e., the degree to which spring 19 compresses) may be indicated on a scale 26 engraved or otherwise marked on the forward end (toward the left end as shown) of the outer diameter of bar 20.

Connected to a forward side of the base member 12 is a flexible, expandable annular pressure bladder 34 defining a generally conical, central casting area 32 and extendable axially forward from the base member 12 over a length of the bladder 34. The bladder 34 is configured and dimensioned to extend generally along the length of a residuum covered by a suction socket on which the prosthesis socket material is to be molded. The bladder 34 preferably includes an outer wall 36 that may be formed of a silicone rubber material reinforced with a web or strands of relatively non-stretchable material or a material that limits extension outwardly of the wall 36 or may be formed of an elastomer material such as silicone elastomer with a separate outer covering of material that limits or prevents outward distension of the outer wall 36.

An inner wall 38 of the bladder 34 defining the casting area 32 may be formed of one or more sheets of pliable and complaint sheet material that also may be reinforced with elements that permit tailoring the extensibility of the material according to predetermined criteria. In accordance with the preferred embodiment, the inner wall 38 and outer wall 36 comprises substantially thin, flexible material that permits the bladder 34 to be rolled on and off the residual limb in a similar fashion to the bladder disclosed in U.S. Pat. No. 5,885,509 to permit easy donning and doffing of the bladder 34 over the residual limb. A preferred characteristic of the inner wall 38 of the bladder 34 is that it is formed of a material that will not itself distend substantially when tensioned, yet will be fully compliant when the chamber behind it expands to envelop a residual limb and prosthesis socket molding material that are located within the casting area 32.

In accordance with a preferred embodiment of the invention, the inner wall 38 of bladder 34 is formed from a thin sheet material that is separate from the outer wall 36 and bonded or otherwise attached thereto in a manner defining expandable chambers between the inner wall 38 and the outer wall 36. The inner wall 38 may be stitched, heat sealed, bonded or otherwise firmly secured to the inner periphery of the outer wall 36 to define the multiple expandable chambers 40, 42 and 44. The chambers 40, 42 and 44 extend along the length of the bladder 34 and peripherally surround the central casting area 32. The chambers 40, 42 and 44 typically are expandable when pressurized with fluid such as air to cause the inner walls 38 of the chambers to expand inwardly toward the central casting area 32 to exert pressure on a prosthesis socket material to be molded within the bladder 34.

The connector 14, as shown in FIG. 4, includes at least one fluid passage 64 and a pin release mechanism (not shown) for releasing pin 28 from the lock device 16 in a manner known in the art. The fluid passage or passages 64 communicates with appropriate ports and conduits in connector 14 and base 12 that are in communication with the interiors of the chambers 40, 42 and 44 to permit pressurized fluid to be supplied to the interiors of the chambers. The fluid passage 64 may be connected with the base 12 instead of the connector 14, if desired. Any other suitable arrangement may be utilized to permit passage of pressurized fluid from a location outside the chambers 40, 42, 44 to the interiors thereof. Indeed, if the option is chosen to utilize the handle 22 as an extension device to apply tractive force to pin 28 which may cause connector 14 to separate from base 12, the fluid passage 64 would be oriented and arranged so as to permit continuous supply of pressurized fluid to the interiors of the chambers 40, 42 and 44 while tractive force is applied to pin 28.

The chambers 40, 42 and 44 also could be molded into the sidewall 36, with the inner walls of the sidewall 36 being formed so they are distendable radially inwardly at the inner sides of the chambers 40, 42, 44. In this form, the chambers could be defined by a one-piece sidewall having expandable pockets defining the expandable chambers.

A first embodiment of the bladder 34 is illustrated in FIGS. 5A–5D where inner and outer walls 36, 38 define extendable chambers 40, 42 and 44 extending axially along the length of the bladder 34 and circumferentially surrounding the central casting area of 32. The inner wall 38 of the bladder 34 includes non-expandable regions disposed between the chambers 40, 42 and 44 where the inner and outer walls 36, 38 are firmly secured to each other such as by stitching, heat sealing, bonding or the like, such as shown at 39 in FIG. 5D.

The bladder 34 includes a proximal end 35 and a distal end 37, with the proximal end 35 having a smaller diameter than the distal end 37, although the bladder also could be generally cylindrical in form depending on the shape of the socket and the residuum. The length of the bladder 34 is selected so that it will envelop a residuum and prosthesis socket casting material located on the distal end area of the residuum. If desired, a plurality of bladders may be made in several lengths having appropriate minor and major diameters to accommodate various size residuums.

The inner wall 38 is secured to the outer wall 36 along longitudinal seams such as shown at 39 and may be made of a stretchable elastic material or a material that has limited elasticity, provided that the inner wall 38 may distend radially toward the casting area of 32 to a degree sufficient to exert sufficient radial compressive force on casting material located on a residuum that has been placed on the casting area 32. If the inner wall 38 is of limited elasticity, sufficient excess inner wall material will be provided to enable the inside wall to bow inwardly toward the central casting area when the expandable chamber defined by the inner wall is expanded with pressurized fluid.

The arrangement of the inner chambers 40, 42 and 44 can be seen in FIGS. 5B, 5C, and 5D.

Fluid passageways 66 may be integrally molded, configured between the walls 36, 38, or otherwise provided in the proximal end structure 35 of the bladder 34, as shown in FIGS. 5B and 5C. These passageways communicate with fluid passage or passageways 64 associated with connector 14 or base 12, as previously described. Preferably, each expandable chamber 40, 42 and 44 is provided with an independent fluid passageways 66, although the chambers may be mutually connected if desired so that they will be each exposed to the same internal pressure. Alternatively, the chambers 40, 42 and 44 may be pressurized independently through a series of fluid passageways associated with the connector 14 or the base 12. The passageways may be separate and distinct conduits located inwardly or outwardly of outer wall 36. It is also contemplated that fluid conduits may be incorporated in or through the walls of the bladder 34 directly if desired without passing through the base 12 or connector 14.

As illustrated in FIGS. 5A–5D, the outer wall 36 generally retains its shape both before and after the chambers 40, 42 and 44 are pressurized. This is due to the outer wall 36 as being formed of a material that limits or prevents outward distension thereof when the chambers are pressurized.

When the expandable chambers 40, 42 and 44 are subjected to internal pressurized fluid such as air, they will expand or be driven to the positions shown in hidden lines in FIG. 5D.

Although not illustrated, the chambers 40, 42 and 44 may be subdivided into a plurality of additional connected or independent chambers that may be divided axially along the length of the bladder 34 to provide additional expandable chambers for selectively pressurizing various regions of a residuum and prosthesis casting material during casting of a prosthesis socket using the casting device of this invention.

Also, the expandible chambers could be molded into a single thickness sidewall of the bladder 34, 34' provided that the innermost wall of the chamber is expandable into the casting area.

Figure 6B:
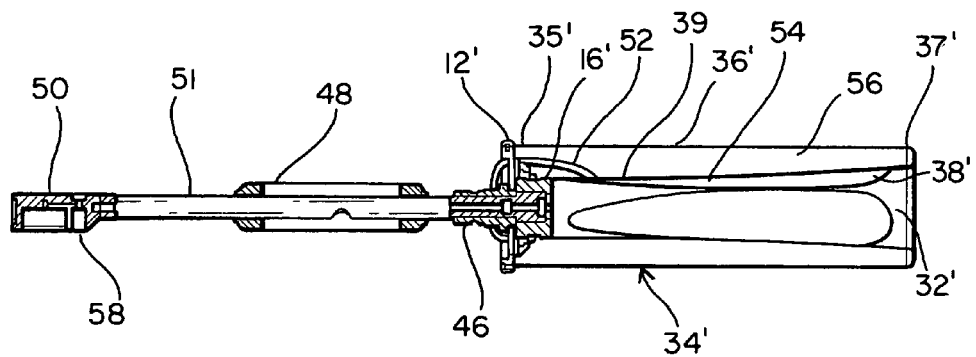
FIG. 6B is a sectional view taken along line VI—VI of FIG. 6A.
Figure 6C:
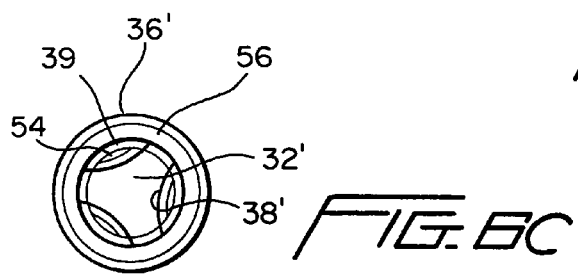
FIG. 6C is a cross-sectional view taken along line VII—VII of FIG. 6A.

FIGS. 6A–6C illustrate an alternate embodiment of the invention wherein a bladder 34' having proximal and distal ends 35', 37' is generally cylindrical in cross-section and includes an outer wall 36' and an inner wall 38' defining multiple expandable inner chambers 54 and an annular outer chamber 56, extending over the inner chambers 54 as seen in FIG. 6C. An additional intermediate annular wall 39 spaced inwardly from the outer wall 36' and outwardly of inner wall 38' defines the outer chamber 56 which in this embodiment is similar to the annular pressure chamber described in U.S. Pat. No. 5,885,509. The side walls 38' and 39 are relatively pliable and compliant to enable the bladder 34' to be easily rolled on or rolled off a residuum and a prosthesis casting material located on the distal end of the residuum so that the casting material may be located within the generally conical casting area 32' defining by the side walls 39. The distension characteristics of intermediate wall 39 are selected to distribute desired casting pressure on the residuum and to distribute pressure loading behind the expandable chambers 54. The outer wall 36' also could be provided with a covering or otherwise be constructed so that its distention under internal pressure in the chambers 54, 56 is limited.

A base 12' contains appropriate valving, tubes and conduits enabling distribution of pressurized fluid to the chambers 54 and 56 to enable them to be selectively pressurized independently or collectively to cause inward expansion of the inner walls of the chambers to compress a settable prosthesis socket material in the casting area 32 and 32'. Combination handle and pump 48, 51 is connected to the base 12' through a connector 46 and a pressure indicator 50 may be provided to indicate pressure within the chambers 54, 56. The pump 48, 51 is similar to the pump described in U.S. Pat. No. 5,885,509, to which reference may be made for a fuller description of the pump.

Figure 7:
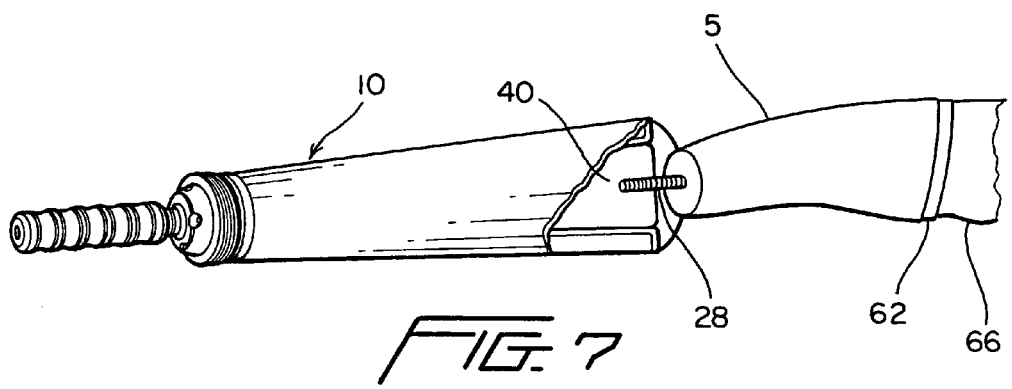
FIG. 7 is a perspective view showing the prosthetic socket casting device of FIG. 1 after separation from a prosthesis socket and residuum upon completion of a casting procedure.

FIG. 7 illustrates the embodiment of the casting device illustrated in FIGS. 1 and 2 in relation to a residuum 66, a suction socket 62, a molded prosthesis socket 5 and a locking pin 28 extended from the suction socket 62 through the distal end of the socket 5. FIG. 7 depicts the relationship of the depicted elements upon removal of the casting device 10 from the prosthesis socket 5 after completion of the casting of the socket 5 and after at least partial curing and hardening of the socket 5.

In a manner known in the art, the socket 5 is then removed from the suction socket 62 for final finishing and the suction sleeve 62 is removed from the residuum 66. The locking pin 28, of course, may be removed any time by unthreading it from the distal end of the suction sleeve 62.

In operation, the residuum is prepared for casting a prosthesis pre-formed casting material, for example as described in U.S. Pat. No. 5,718,925, by first placing a suction socket 62 and a locking pin 28 on the distal end of the residuum, which also may be prepared with any other protective layer beneath the suction sleeve.

The bladder 34 is unfurled from a folded or retracted position on the base forwardly over the distal end of the residuum 62 with the casting material thereon as described for example in U.S. Pat. No. 5,885,509. The locking pin 28 may be previously coupled to the base 12 before the bladder is unfurled. The expandable chambers are then pressurized with an appropriate fluid such as air or other medium. The chambers will expand radially inwardly toward the casting area 32, 32' where the prosthesis socket material and residuum are located. The bladder 34, 34' is supported partly at least by the residuum as the inflatable chambers 40, 42 and 44 and chambers 54, 56 are expanded. Prosthetists, if conditions warrant, may impose additional pressure and manipulation in selected locations on the residuum through the bladder and the chambers to control the shape and form of the prosthesis socket material before it is hardened. The prosthesis socket material is selected to be settable or curable into a hardened condition while pressurized by the bladder 34, 34' and its associated expandable chambers. The orientation, location and configuration of the various expandable chambers, 40, 42, 44, 54 and 56 are selected to produce a desirable pressure distribution over the periphery of the prosthesis socket material while it sets into a hardened condition. For example, the use of three peripherally spaced inflatable chambers has been found to produce desirable pressure distributions for casting a prosthesis socket material on a residual limb.

As described in U.S. Pat. No. 5,885,509, anchoring the locking pin 28 relative to the base 12 during casting results in a reactive tractive force being applied to the distal end of a suction socket 62 containing the residuum on which the prosthesis socket material is applied. Such tractive force is highly desirable and elongates the distal end area of the residuum in a manner resulting in a highly accurate formation of a prosthesis socket internal volume while it is compressed against the residuum. As compared with the single annular expandable chamber used in prior art devices, the multiple expandable chambers distribute casting pressure on the prosthesis socket material in a non-cylindrical pattern that more closely follows the anatomical contours of the typical residuum.

The specific embodiments of the invention described herein are intended to be illustrative only and various modifications thereto may be envisioned and implemented by a person skilled in the art without departing from the spirit and scope of the invention which is defined in the claims that follow.

I claim:

1. A prosthesis socket direct casting device comprising:
   a base having a forward side;
   an elongated flexible annular bladder defining a generally conical interior casting area carried by the base and extendable from the forward side thereof;
   said bladder containing a plurality of circumferentially spaced expandable chambers extending generally along the length of the casting area;
   said chambers comprising closed interior volumes defined at least in part by inner walls extendable only radially inwardly towards the casting area;
   said base including at least one pressurized fluid supply passage in communication with the interior volumes of said chambers;
   said bladder having an open end opposite the end connected to the base;
   said open end providing access to the casting area.

2. A prosthetic socket direct casting device as claimed in claim 1, including three circumferentially spaced expandable chambers.

3. A prosthetic socket direct casting device as claimed in claim 1, including a distention limiting structure associated with at least one inner wall of said bladder that limits radially outward distension thereof.

4. A prosthetic socket direct casting device as claimed in claim 1, including an additional expandable chamber located intermediate said expandable chambers and an outer wall of said bladder.

5. A method of direct pressure casting a prosthesis socket material on a residuum comprising the steps:
   distributing an uncured settable prosthesis socket material on the distal end area of a residuum;
   locating the residuum and said prosthesis socket settable material in a generally conical central casting area defined by an annular flexible bladder containing a plurality of longitudinally extending expandable chambers that expand only radially inwardly of the bladder upon pressurization;
   pressurizing the multiple chambers to cause them to expand radially inwardly toward the casting area to thereby apply pressure on the outer periphery of the prosthesis socket casting material along circumferentially separated zones.

6. The method of direct casting a prosthesis socket material as claimed in claim 5, including restraining the distal end area of the residuum relative to a base element to which one end of the bladder is secured such that reactive loads imposed on the residuum during pressurization of the chambers tending to compress the prosthesis socket material and to drive the residuum away from the base element is reacted into the base element and the distal end area of the residuum to thereby produce a tractive force against the distal end area of the residuum during pressurization and compression of the prosthesis socket material.

7. The method of direct casting a prosthesis socket material as claimed in claim 6, including using a suction socket applied to the residuum under the prosthesis socket material and an associated locking pin connected to the base element to restrain the distal end of the residuum during compression of the prosthesis socket material.

8. A prosthesis socket direct casting device comprising:
   a base having a forward side;

an elongated flexible annular bladder defining an interior casting area carried by the base and extendable from the forward side thereof;

said bladder containing a plurality of circumferentially spaced expandable chambers extending generally along the length of the casting area;

said chambers comprising closed interior volumes defined at least in part by inner walls extendable radially inwardly towards the a casting area;

said base including at least one pressurized fluid supply passage in communication with the interior volumes of said chambers;

said bladder having an open end opposite the end connected to the base;

said open end providing access to the casting area;

said bladder having an outer periphery with a distension limiting structure associated with at least one of the inner walls, the distension limiting structure preventing radially outward distension of the bladder to thereby maintain the outer periphery generally constant when the chambers are in both expanded and non-expanded conditions.

* * * * *